(12) United States Patent
Hoffman

(10) Patent No.: US 7,112,798 B2
(45) Date of Patent: Sep. 26, 2006

(54) TAILORABLE CT-DETECTOR ASSEMBLY

(75) Inventor: David M. Hoffman, New Berlin, WI (US)

(73) Assignee: General Electric Company, Schenectady, NY (US)

( * ) Notice: Subject to any disclaimer, the term of this patent is extended or adjusted under 35 U.S.C. 154(b) by 365 days.

(21) Appl. No.: 10/707,600

(22) Filed: Dec. 23, 2003

(65) Prior Publication Data

US 2005/0135563 A1    Jun. 23, 2005

(51) Int. Cl.
*G21K 1/02*    (2006.01)
(52) U.S. Cl. .................................. 250/363.1
(58) Field of Classification Search ............... 250/367, 250/363.1
See application file for complete search history.

(56) References Cited

U.S. PATENT DOCUMENTS

| 4,180,737 | A | * | 12/1979 | Kingsley | .................... 250/367 |
| 4,856,041 | A | * | 8/1989 | Klein et al. | .................. 378/147 |
| 5,025,462 | A | * | 6/1991 | Saito et al. | .................... 378/19 |
| 5,033,074 | A | * | 7/1991 | Cotter et al. | ................. 378/147 |
| 5,099,134 | A | * | 3/1992 | Hase et al. | ............... 250/505.1 |
| 6,091,795 | A | * | 7/2000 | Schafer et al. | ................. 378/19 |
| 6,553,092 | B1 | * | 4/2003 | Mattson et al. | ................ 378/19 |
| 2004/0217291 | A1 | * | 11/2004 | Hoge | ....................... 250/363.1 |
| 2005/0017182 | A1 | * | 1/2005 | Joung et al. | ............. 250/363.1 |

* cited by examiner

*Primary Examiner*—David Porta
*Assistant Examiner*—Marcus Taningco
(74) *Attorney, Agent, or Firm*—General Electric Company

(57) ABSTRACT

An imaging detector assembly is provided comprising a detector array and a scintillator assembly positioned in communication with the detector array. The imaging detector assembly further includes a first collimator array optimized to shield the scintillator assembly. The first collimator array is mounted to the scintillator assembly. The imaging detector assembly further includes a second collimator array optimized to reduce x-ray scatter. The second collimator array is mounted independently from the first collimator array.

16 Claims, 3 Drawing Sheets

TAILORABLE CT-DETECTOR ASSEMBLY

BACKGROUND OF INVENTION

The present invention relates generally to a detector assembly, and, more particularly to a two piece collimator assembly with improved design flexibility.

Computed tomography has been utilized for a wide variety of imaging applications. One such category of applications is comprised of medical imaging. Although it is known that computed tomography may take on a wide variety of configurations within the medical industry, it commonly is based on the transmission of low energy rays through a body structure. These low energy rays are subsequently received and processed to formulate an image, often three-dimensional, of the body structure that can by analyzed by clinicians as a diagnostic aid.

The reception of the low energy rays, such as gamma rays or x-rays, is often accomplished through the use of a device referred to as a detector assembly. The detector assembly is typically comprised of a plurality of structures working in concert to receive and process the incoming energy rays after they have passed through the body structure. The detector assembly utilizes scintillator to absorb the photons and convert their energy into visible light. This allows the low energy rays received by the scintillator detector to be converted into useful information. Scintillator elements may come in a wide variety of forms and may be adapted to receive a wide variety of incoming rays. The light produced by the scintillator element is commonly processed by way of a device such as a light sensitive photodiode, which converts the light from the scintillator element into an electronic signal. In this fashion, the information from the scintillator detector can be easily transferred, converted, and processed by electronic modules to facilitate viewing and manipulation by clinicians.

Imaging assemblies additionally include an element referred to as a collimator. A collimator is an element that commonly incorporates two fundamental functions. The collimator is used to reduce x-ray scatter as the x-rays approach the scintillator element. Scattered photons can cause noise and reduce resolution causing image artifacts. In addition, the collimator is commonly used as a shielding device for shielding the edges of the individual scintillator cells. This is necessary to prevent, X-rays from impinging on the edges of the scintillators causing non linearities and image artifacts, x-rays from damaging the reflector between scintillator elements, X-rays being transmitted through the gap between scintillator elements and impinging on the photo diode causing noise or X-rays being transmitted through the gap between scintillator elements and impinging on electronics located behind the detector causing damage to these sensitive electronic components. Thus present collimator designs commonly attempt to balance shielding and scatter reducing properties.

Unfortunately, the design characteristics that make a collimator optimal for shielding the scintillator edges are not always compatible with the characteristics that make a collimator optimal for reducing x-ray scatter. Present collimator formation, therefore, often relies on a functional compromise between these two competing characteristics. Even when the physical characteristics necessary to perform each of these functions is not directly incompatible, their importance may vary by function. High manufacturing and assembly tolerances are often important for proper shielding functionality. These high tolerances, however, are not commonly required to reduce x-ray scatter. Therefore, by requiring the collimator assembly to be manufactured with tolerances suitable for shielding, the cost of the entire assembly is often increased.

Approaches to resolving this balance of characteristics has lead some to modify other aspects of the detector assembly to accommodate existing collimator designs. These approaches include leaving large gaps between adjoining scintillator elements; use of x-ray absorbing layers between scintillator cells; and the use of organic reflector composites. In these approaches, however, the distance between scintillator elements tends to be large. This is often incompatible with the small cell and small gap requirements for the current generation of multi-slice CT systems. In addition, many existing systems do a poor job of attenuating scatter x-rays within the scintillator elements or to prevent X-rays from crossing over from one scintillator cell to an adjoining cell. Thus considerable room for improvement of existing designs and design approaches exists.

It would, however, be highly desirable to have a detector assembly that could be simultaneously optimized for reducing scattering x-rays in addition to shielding scintillator elements. Similarly, it would be highly desirable to have a detector assembly suitable for use in modern high density imaging applications.

SUMMARY OF INVENTION

An imaging detector assembly is provided comprising a detector array and a scintillator assembly positioned in communication with the detector array. The imaging detector assembly further includes a first collimator array optimized to shield the scintillator assembly. The first collimator array is mounted to the scintillator assembly. The imaging detector assembly further includes a second collimator array optimized to reduce x-ray scatter. The second collimator array is mounted independently from the first collimator array.

Other features of the present invention will become apparent when viewed in light of the detailed description of the preferred embodiment when taken in conjunction with the attached drawings and appended claims.

DETAILED DESCRIPTION

Figure 1:
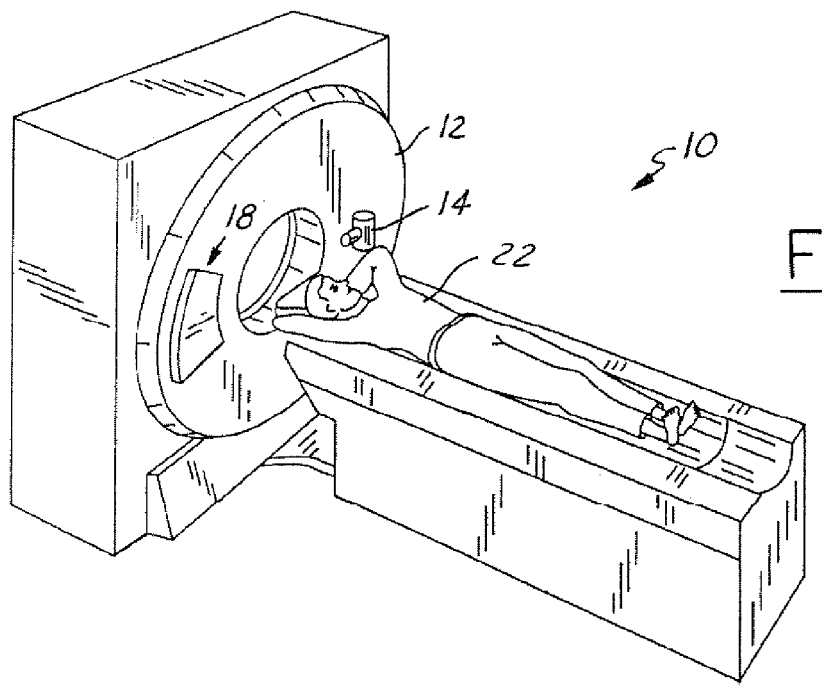
FIG. 1 is an illustration computed tomography imaging system for use in the present invention.
Figure 2:
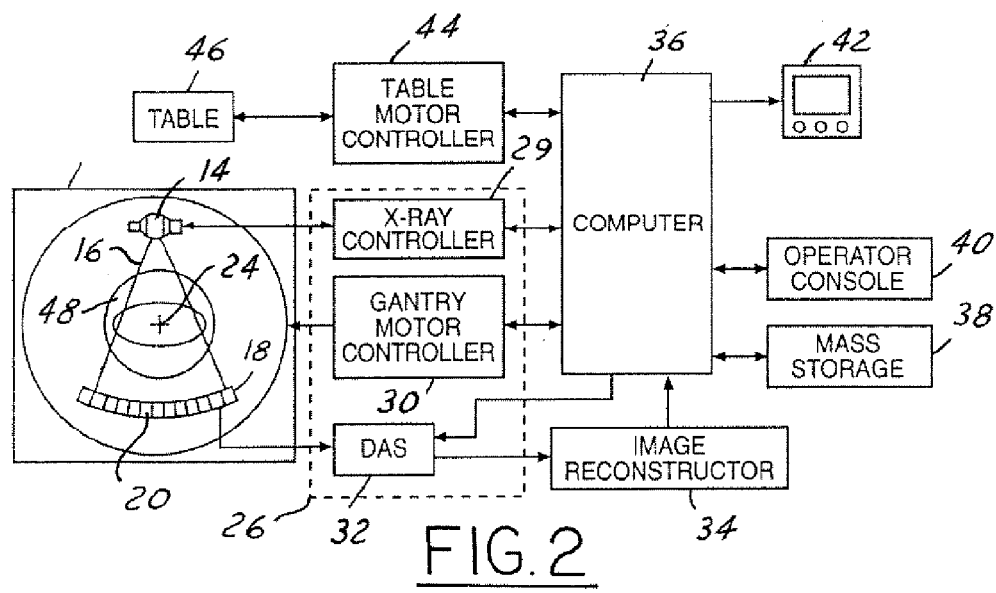
FIG. 2 is a block diagram of the imaging system illustrated in FIG. 1.

Referring now to FIGS. 1 and 2, which are illustrations of a computed tomography (CT) imaging system 10 for use with the detector assembly 18 of the present invention. Although a particular CT imaging system 10 has been illustrated, it should be understood that the detector assembly 18 of the present invention could be utilized in a wide variety of imaging systems. The CT imaging system 10 includes a scanner assembly 12 illustrated as a gantry assembly. The scanner assembly 12 includes an x-ray source 14 for projecting a beam of x-rays 16 toward a detector assembly 18 positioned opposite the x-ray source 14. The detector assembly 18 includes a plurality of detector elements 20, referred to as a detector array, which combine to sense the projected x-rays 16 that pass through an object, such as a medical patient 22. Each of the plurality of detector elements 20 produces an electrical signal that represents the intensity of an impinging x-ray beam and hence the attenuation of the beam 16 as it passes through the object of patient 22. Commonly, during a scan to acquire x-ray projection data, the scanner assembly 12 is rotated about the center of rotation 24. In one embodiment, illustrated in FIG. 2, detector elements 20 are arranged in one row such that projection data corresponding to a single image slice is acquired during a scan. In other embodiments, the detector elements 20 can be arranged in a plurality of parallel rows, such that projection data corresponding to a plurality of parallel slices can be acquired simultaneously during a scan.

The rotation of the scanner assembly 12 and the operation of the x-ray source 14 are preferably governed by a control mechanism 26. The control mechanism 26 preferably includes an x-ray controller 29 that provides power and timing signals to the x-ray source 14 and a scanner motor controller 30 that controls the rotational speed and position of the scanner assembly 12. A data acquisition system (DAS) 32 in control mechanism 26 samples analog data from the detector elements 20, commonly a photodetector array, and converts the data to digital signals for subsequent processing. An image reconstructor 34 receives sampled and digitized x-ray data from DAS 32 and performs high speed image reconstruction. The reconstructed image is applied as an input to a computer 36 which stores the image in a mass storage device 38.

The computer 36 also can receive commands and scanning parameters from an operator via console 40 that has a keyboard or similar input device. An associated display 42 allows the operator to observe the reconstructed image and other data from the computer 36. The operator supplied commands and parameters are used by computer 36 to provide control signals and information to the DAS 32, x-ray controller 29, and scanner motor controller 30. In addition, the computer 36 operates a table motor controller 44 which controls a motorized table 46 to position patient 22 within the scanner assembly 12. Particularly, the table 46 moves portions of the patient 22 through the scanner opening 48.

Figure 3:
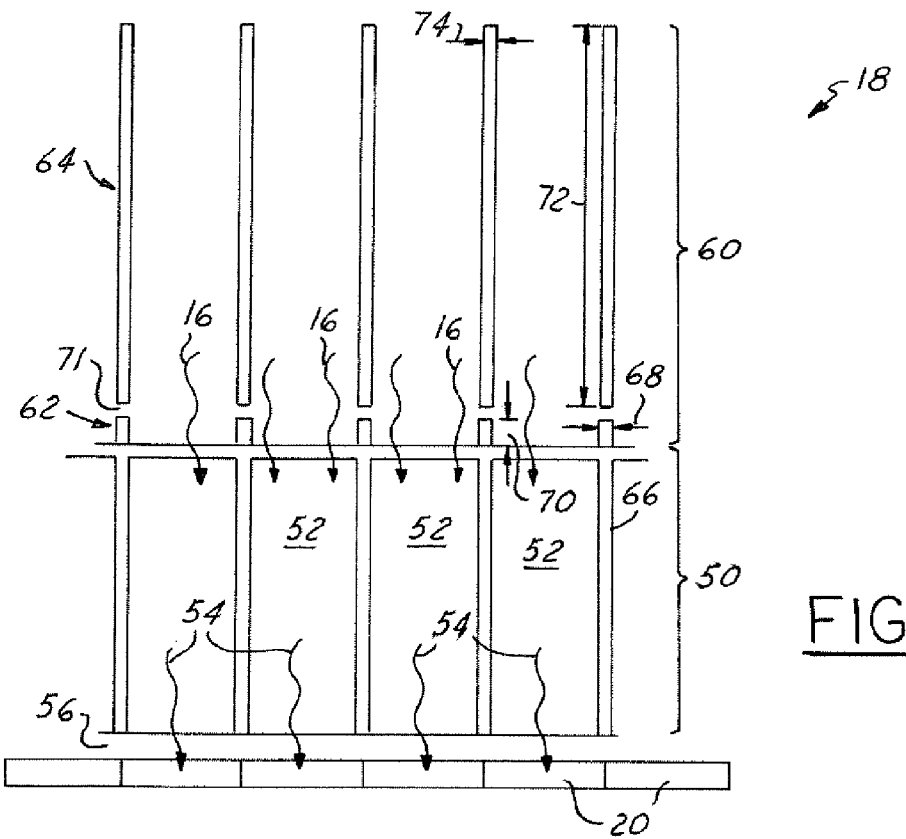
FIG. 3 is an illustration of a detector assembly for use in the imaging system illustrated in FIG. 1.

Each of the detector elements 20 of the detector assembly 18 produces a separate electrical signal that is a measurement of the beam attenuation at the detector location. As illustrated in FIG. 3, the detector assembly 18 includes a scintillator assembly 50 including plurality of scintillator elements 52 each of which is associated with one of the detector elements 20. Scintillator elements 52 are known devices that, when struck by x-rays, convert at least a portion of the energy of the x-rays 16 into light 54 that can be detected by the detector elements 20, commonly photodetectors. The photodetectors 20, such as photodiodes or photocells, are commonly optically coupled, using an optical coupler 56, to the backs of the scintillator elements 52 and are utilized to generate electrical signals representative of the light output from the scintillator elements 50. The attenuation measurements from all detector elements 20 in the detector assembly 18 are acquired separately to produce a transmission profile. It should be understood that FIG. 3 illustrates a cross-section of the detector assembly 18 and is intended to be representative of both linear and multi-dimensional arrays of detectors.

Figure 4:
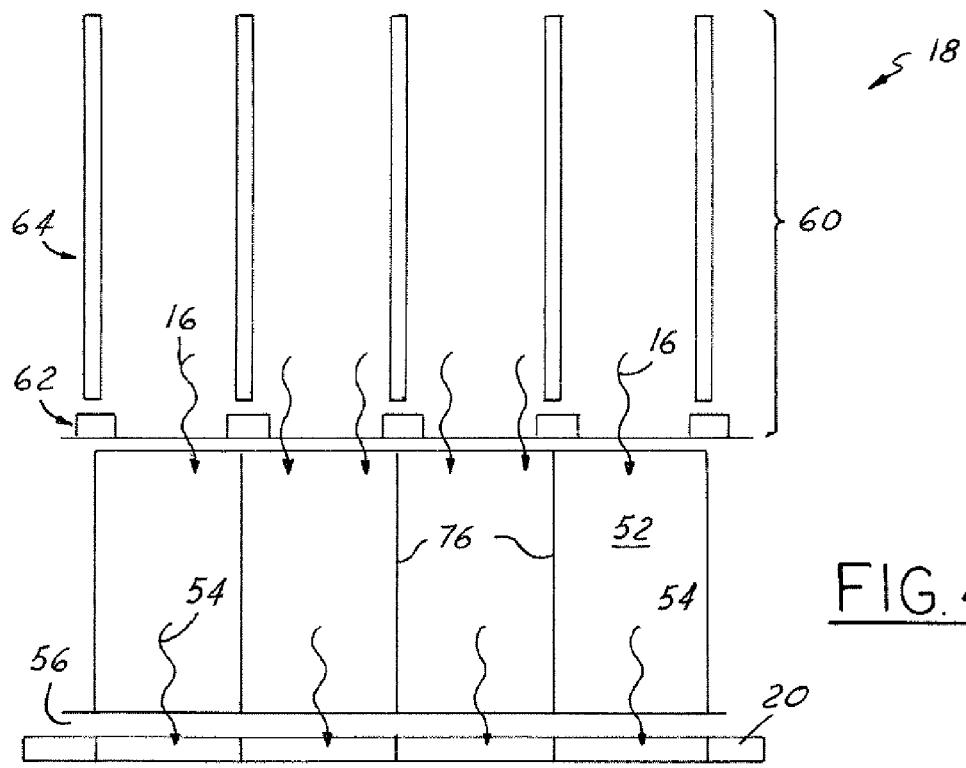
FIG. 4 is an alternate embodiment of a detector assembly for use in the imaging system illustrated in FIG. 1.

The present invention provides a unique approach to collimation of the incoming x-rays 16 by including a collimator assembly 60 comprised of a first collimator array 62 and a second collimator array 64. The use of such a two piece collimator assembly 60 allows each individual collimator array 62,64 to be specifically tailored and optimized for a single function rather than requiring a single collimator to balance differing performance requirements. To this end, the present invention includes a first collimator array 62 optimized to shield the scintillator array 50. Specifically, the first collimator array 62 is optimized to shield the scintillator element edges 66. Various methods of optimizing a collimator assembly to shield the scintillator array 50 would be obvious. The first collimator array 62 may be formed from a material highly suitable for shielding such as a high-Z, high atomic number material. The first collimator array 62 may have an increased first collimator width 68 (see FIG. 4) such as a width greater than said second collimator width 74. The first collimator height 70 is preferably minimal such that the first collimator array 62 retains a low profile and has little effect on x-ray scatter.

Figure 5:
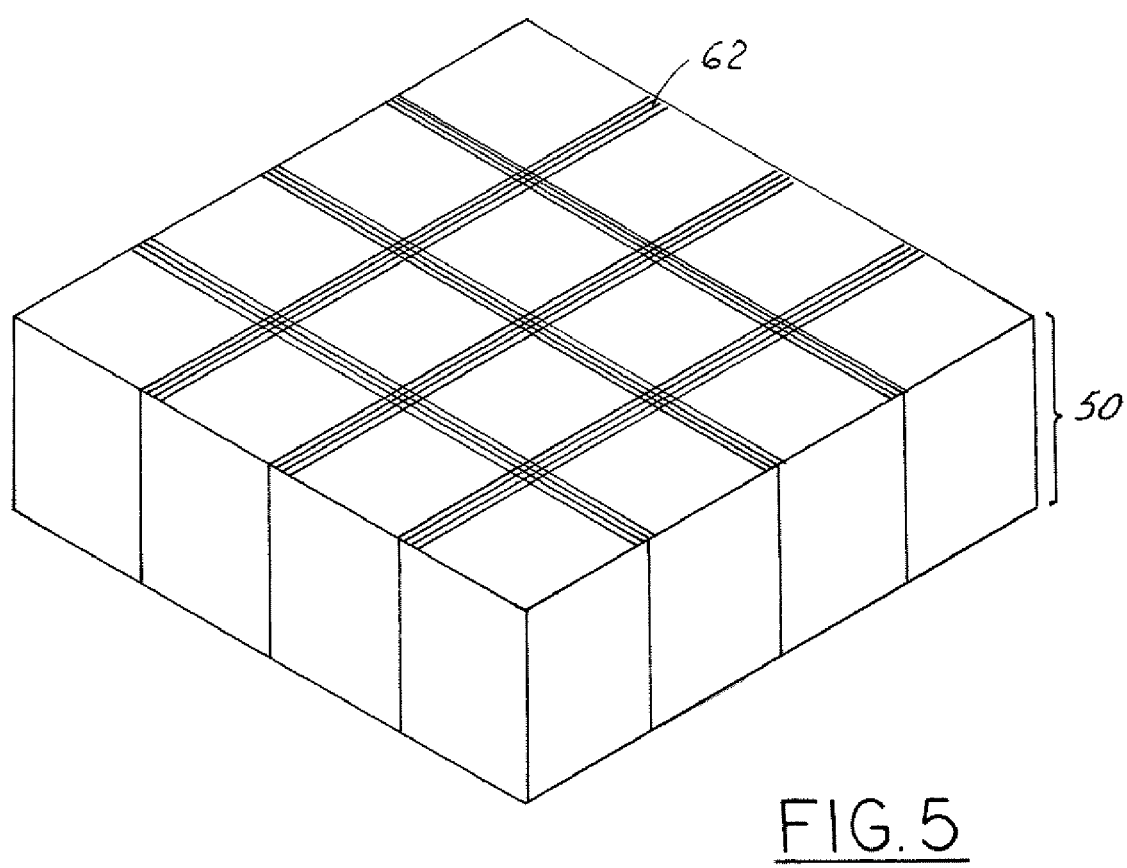
FIG. 5 is an illustration of a detector assembly for use in the imaging system illustrated in FIG. 1, the first collimator array illustrated etched onto the scintillator assembly.

The first collimator array 62 can be formed in a variety of fashions and materials. It can be formed from composite materials. It may be formed from cast materials. In one embodiment, it is contemplated that the first collimator array 62 can be formed with reduced manufacturing tolerances. In this fashions, the increased cost and manufacturing difficulty can be limited to the first collimator array 62 where such tolerances are beneficial. The first collimator array 62 may further be designed to optimize quantum detection efficiency QDE by providing minimal x-ray blockage (see FIG. 3). It is contemplated that the first collimator array 62 can be formed directly onto the scintillator array 50 to improve accuracy of placement. The first collimator array 62 can be cast directly onto the scintillator array 50 with a wide variety of materials such as loaded epoxies, lead, lead alloys, or composites. In other embodiments it is contemplated that the first collimator array 62 can be formed directly onto the scintillator array 50 (see FIG. 5) using a grid. This grid may include an etched grid, a grid formed by plunge electron discharge machining (EDM'ing), or a cross-wire grid. The low aspect ratio and direct fabrication allow a precise location of the first collimator array 62 in relation the scintillator elements 52 and reflector gaps 58 (Not shown in the figure). This allows less material to be used in the first collimator array 62, which in turn reduces x-ray blockage and increases QDE or lowers the patient dose.

The present invention further includes a second collimator array 64 optimized to reduce x-ray scatter. It is contemplated that the second collimator array 64 be designed to have only minimal effect on shielding. In this fashion the second collimator array 64 can be directly tailored to the task of x-ray scatter reduction without impacting shielding. The second collimator array 64 is preferably manufactured and mounted independently from the first collimator array 62. This allows the manufacturing, materials, and assembly methods to remain independent. Although a mounting gap 71 between the first collimator array 62 and the second collimator array 64 is not required, one embodiment contemplates a gap of approximately one millimeter. The second collimator array 64 can be optimized to reduce scatter in a variety of fashions. A high aspect ratio, a second collimator height 72 maximized and a second collimator width 74 minimized (less than 200 microns), allows the second collimator array 64 to reduce scatter with minimal effect on shielding.

Figure 6:
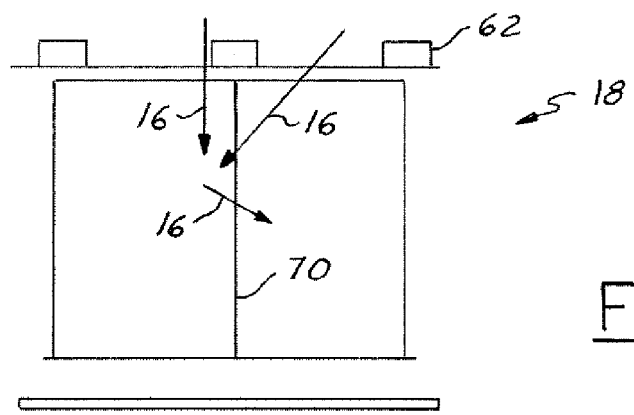
FIG. 6 is an alternate embodiment of a detector assembly for use in a $4^{th}$ generation imaging system or an imaging system similar to the one illustrated in FIG. 1, but with a stationary detector ring that completely or mostly saurrounds the patient.

The second collimator array 64 can be manufactured in a variety of fashions to optimize for reduction in scatter. The second collimator array 64 may be cast, formed from composites, use traditional plate technology, or adopt any other manufacturing technology. Since the second collimator array 64 is optimized solely for scatter reduction, the second collimator array 64 can be manufactured with much greater tolerances than are typically acceptable for shielding purposes. This allows a reduction in manufacturing time, complexity, and cost for the overall collimator assembly 60. In addition, since the second collimator array 64 can be manufactured without concern for engagement of the first collimator array 62, it can be designed to improve detector QDE and improve cell low signal performance. Finally, an added advantage of the present detector assembly 18 is that the second collimator array 64, due to independent mounting, can be easily removed such that the detector assembly can be installed into fourth generation imaging systems wherein x-rays 16 are received from a variety of angles (see FIG. 6).

The present invention not only provides an improved approach and design for detector assemblies 18 in regards to improved collimation. The present design also allows for the use of higher performing scintillator assemblies 50. Since the first collimator array 62 can be directly tailored to shielding and can be mounted or formed directly onto the scintillator array 50, the amount of X-ray cross-talk within the individual scintillator elements 52 can be significantly reduced. If the scintillator elements 52 are separated only by thin film reflectors 76 then the x-ray shielded portion 77 of the scintillator element becomes an X-ray attenuator to shield X-rays 16 that are scattered in one scintillator cell 52 from crossing over from one scintillator cell 52 to an adjoining scintillator cell. By varying the first collimator width 68 of the first collimator array, the amount of X-ray shielding can be tailored to optimize the performance of the detector 10 or varying the amount of X-ray shielding from cell to cell. A reduction in X-ray cross talk will improve the spatial resolution of the CT system. By removing the necessity for x-ray blocking gaps or layers, the scintillator elements 52 can be positioned closer to each other and thereby improve resolution of the detector assembly 18.

While particular embodiments of the invention have been shown and described, numerous variations and alternative embodiments will occur to those skilled in the art. Accordingly, it is intended that the invention be limited only in terms of the appended claims.

The invention claimed is:

1. An imaging detector assembly comprising:
a detector array;
a scintillator assembly positioned in communication with said detector array;
a first collimator array optimized to shield said scintillator assembly, said first collimator array mounted to said scintillator assembly; and
a second collimator array optimized to reduce x-ray scatter, said second collimator array mounted independently from said first collimator array.

2. An imaging detector assembly as described in claim 1, wherein said first collimator array has a first collimator width optimized to shield said scintillator and a first collimator height with minimal effect on said x-ray scatter.

3. An imaging detector assembly as described in claim 1, wherein said second collimator array has a second collimator height optimized to reduce said x-ray scatter and a second collimator width with minimal effect on shielding said scintillator.

4. An imaging detector assembly as described in claim 1, wherein said first collimator array and said second collimator array are comprised of high-Z, high atomic number materials.

5. An imaging detector assembly as described in claim 1, wherein said first collimator array is comprises of a material optimized to shield said scintillator.

6. An imaging detector assembly as described in claim 1, wherein said second collimator array is comprised of a material optimized to reduce x-ray scatter.

7. An imaging detector assembly as described in claim 1, wherein said second collimator width is less than 200 microns; and
said first collimator width is greater or equal to said second collimator width.

8. An imaging detector assembly as described in claim 1, wherein said first collimator array is comprised of a loaded epoxy formed directly onto said scintillator array.

9. An imaging detector assembly as described in claim 1, wherein said first collimator array is comprised of a plunged electron discharge machined grid formed onto said scintillator array.

10. An imaging detector assembly comprising:
a detector array;
a scintillator assembly positioned in communication with said detector array, said scintillator assembly comprised of a plurality of scintillator cells separated only by thin film reflectors;
a first collimator array optimized to shield said scintillator assembly, said first collimator array formed directly onto said scintillator assembly; and
a second collimator array optimized to reduce x-ray scatter, said second collimator array mounted independently from said first collimator array.

11. An imaging detector assembly as described in claim 10, wherein said first collimator array is optimized to improve the quantum detection efficiency of the imaging detector assembly.

12. An imaging detector assembly as described in claim 10, wherein said first collimator array has a first collimator width optimized to shield said scintillator and a first collimator height with minimal effect on said x-ray scatter.

13. A method of forming an imaging detector assembly comprising:
optimizing a first collimator array to generate scintillator shielding properties;
mounting said first collimator array onto a scintillator assembly, said scintillator assembly comprising a plurality of scintillator elements;
optimizing a second collimator array to reduce x-ray scatter;
mounting said second collimator array independently from said first collimator array, said first collimator positioned between said scintillator and said second collimator array.

14. A method of forming an imaging detector assembly as described in claim 13, further comprising:
manufacturing said second collimator array with greater tolerances than said first collimator array.

15. A method of forming an imaging detector assembly as described in claim 13, further comprising:

removing said second collimator array for use in a fourth generation imaging assembly.

16. A method of forming an imaging detector assembly as described in claim 13, further comprising:

separating each of said plurality of scintillator elements only by thin film reflectors; and optimizing a first collimator width to generate an x-ray shielded portion that performs as an x-ray attenuator to reduce x-ray scatter within each of said plurality of scintillator elements.

* * * * *